(12) United States Patent
Kenaschuk

(10) Patent No.: US 6,870,077 B2
(45) Date of Patent: Mar. 22, 2005

(54) HIGH LINOLENIC ACID FLAX

(76) Inventor: Edward O. Kenaschuk, 438 - 15th St., Morden, Manitoba (CA)

( * ) Notice: Subject to any disclaimer, the term of this patent is extended or adjusted under 35 U.S.C. 154(b) by 0 days.

(21) Appl. No.: 10/059,080

(22) Filed: Jan. 30, 2002

(65) Prior Publication Data

US 2003/0159172 A1 Aug. 21, 2003

(51) Int. Cl.[7] ................................................ A01H 5/00
(52) U.S. Cl. ...................................... 800/298; 800/264
(58) Field of Search ................................. 800/264, 298

(56) References Cited

PUBLICATIONS

GRIN Accession PI 91037, National Germplasm Resources Program, USDA, ARS, Jan. 1931.*
GRIN Accession PI 524302, National Germplasm Resources Program, USDA, ARS, 1975.*
Bickert, C., et al "Einsatz der antheren–und mikrosporen-kultur in der züchtung von öllein im hinblick auf eine verbesserung von fettgehalt und–qualitat", *Arbeitstagung der Arbeitsgemeinschaft der Saatzuchtleiter 44,* Nov. 1993; P. 115–121.

Friedt, W., et al "In vitro breeding of high–linolenic, double–haploid lines of linseed (Linum usitatissimum L.) via androgenesis", *Plant Breeding 114,* 1995; P. 322–326.

* cited by examiner

*Primary Examiner*—Elizabeth F. McElwain
(74) *Attorney, Agent, or Firm*—Michael R. Williams; Adrian D. Battison; Ryan W. Dupuis

(57) ABSTRACT

Production of and uses for flax seed having a linolenic acid content of greater than 65% based on total fatty acid content are described.

9 Claims, 4 Drawing Sheets

HIGH LINOLENIC ACID FLAX

FIELD OF THE INVENTION

The present invention relates generally to the field of agriculture. More specifically, the present invention relates to flax seeds, plants and oils having altered fatty acid profiles.

BACKGROUND OF THE INVENTION

Unsaturated fatty acids consist of monosaturates and polyunsaturates (PuFA). There are two classes of PuFA's, omega-3 and omega-6 which are considered as essential fatty acids (EFA) because humans, like all mammals, cannot synthesize them and most obtain them in their diet. Omega-3 is represented by alpha-linolenic acid (LNA) and linseed flax has the highest linolenic content of major seed oils. LNA is metabolized to eicosapentaenoic acid (EPA) and docosahexanoic acid (DHA), increasing the chain length and degree of unsaturation by adding double bonds to the carboxyl group. Humans and animals can convert LNA to EPA and DHA.

Essential fatty acids have several vital functions: they increase metabolic rate, improve metabolism, increase oxygen uptake and increase energy production. EPA and their derivatives are components of membranes surrounding cells; they are required for the transport and metabolism of cholesterol and triglycerides; they are required for normal development of the brain and for brain function in adults; and from EPA's the body makes hormone-like substances called prostaglandins which have important regulating functions in the body, i.e. they regulate arterial muscle tone, sodium excretion through the kidneys, platelet stickness, inflammatory response and immune functions.

In addition to being essential for normal growth and development, omega-3 fatty acids may play an important role in the prevention and treatment of coronary artery disease, hypertension, diabetes, arthritis, and other inflammatory and anti-immune diseases, and cancer.

Linseed flax is grown primarily for its oil which has many industrial uses; manufacture of paints and coatings, oil cloth, printing ink, soap, patent leather, core oils, brake linings, etc. Linseed oil is also used as an anti-spalling and curing agent for concrete surfaces including highways and bridges.

Linseed oil is used as an industrial oil because of its drying property, i.e. ability to dry rapidly to form a durable film upon exposure to air. The drying property of linseed oil is due to the high content of unsaturated fatty acids, particularly linolenic acid. The linolenic content of Canadian flax cultivars varies from 49–42% depending on cultivar and growing conditions. Temperature during seed formation and photoperiod influences the degree of unsaturation of the fatty acid in linseed oil. Cool temperatures and longer photoperiod increases linolenic content. Other factors which may affect the variability of linolenic content are soil moisture, soil fertility and presence of disease.

High linolenic flax oil provides a valuable improved source of omega-3 fatty acid for human nutrition, animal feed and pet foods.

Higher linolenic content of linseed oil is desirable for most of the industrial uses and may result in new industrial uses.

Clearly, there is a need for high linolenic acid flax.

SUMMARY OF THE INVENTION

According to a first aspect of the invention, there is provided a flax seed having a linolenic acid content of greater than 65% of the total fatty acid content of said seed.

According to a second aspect of the invention, there is provided a flax seed that is the product of a plant line designated M5791.

According to a third aspect of the invention, there is provided a flax plant which produces seeds having a linolenic acid content of greater than 65% of the total fatty acid content of said seed.

According to a fourth aspect of the invention, there is provided a flax plant designated M5791.

According to a fifth aspect of the invention, there is provided progeny of a flax plant designated M5791, wherein said progeny produce seeds having a linolenic acid content of greater than 65% of the total fatty acid content of said seed.

According to a sixth aspect of the invention, there are provided seeds from the above-described flax plants.

According to a seventh aspect of the invention, there is provided oil manufactured from the seeds.

According to an eighth aspect of the invention, there is provided a method of producing a flax plant line comprising the steps of:

(a) crossing a plant of a flax plant line designated M5791, or progeny thereof, with an agronomically elite flax plant;

(b) selecting at least one decendant of said cross, said decendant producing seeds having a linolenic acid content of greater than 65% relative to the total fatty acid content of said seed, (c) the flax plant is self-pollinated and, therefore, the linolenic content of seed progeny of M 5791 is stable.

BRIEF DESCRIPTION OF THE DRAWINGS

TABLE 1 shows the fatty acid composition of major seed oils.

TABLE 2 shows fatty acid composition and iodine value of linseed flax and high linolenic flax (M 5791).

TABLE 3 shows the linolenic acid content of Canadian Flaxseed by province.

TABLE 4 shows linolenic acid content of four widely grown Canadian flax cultivars in flax co-operative tests.

TABLE 5 shows the analysis of linolenic acid content of M5791.

TABLE 6 shows the linolenic acid content of M5791 in field scale tests.

Figure 1:
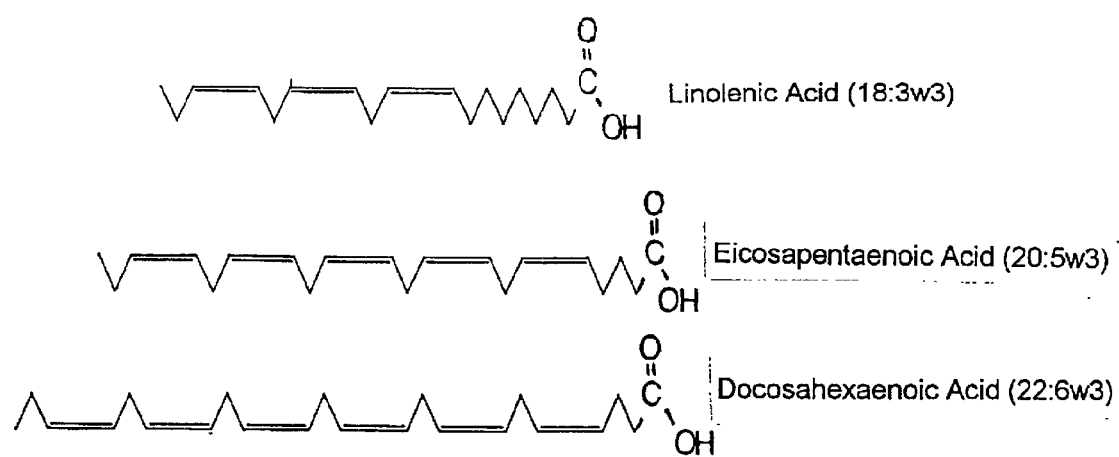

FIG. 1 shows the structural formula for fatty acids. The first number (before the colon) gives the number of carbon atoms in the molecule and the second gives the number of double bonds. $\omega 3$, $\omega 6$, and $\omega 9$ indicate the position of the first double bond in a given fatty acid molecule.

Figure 2:
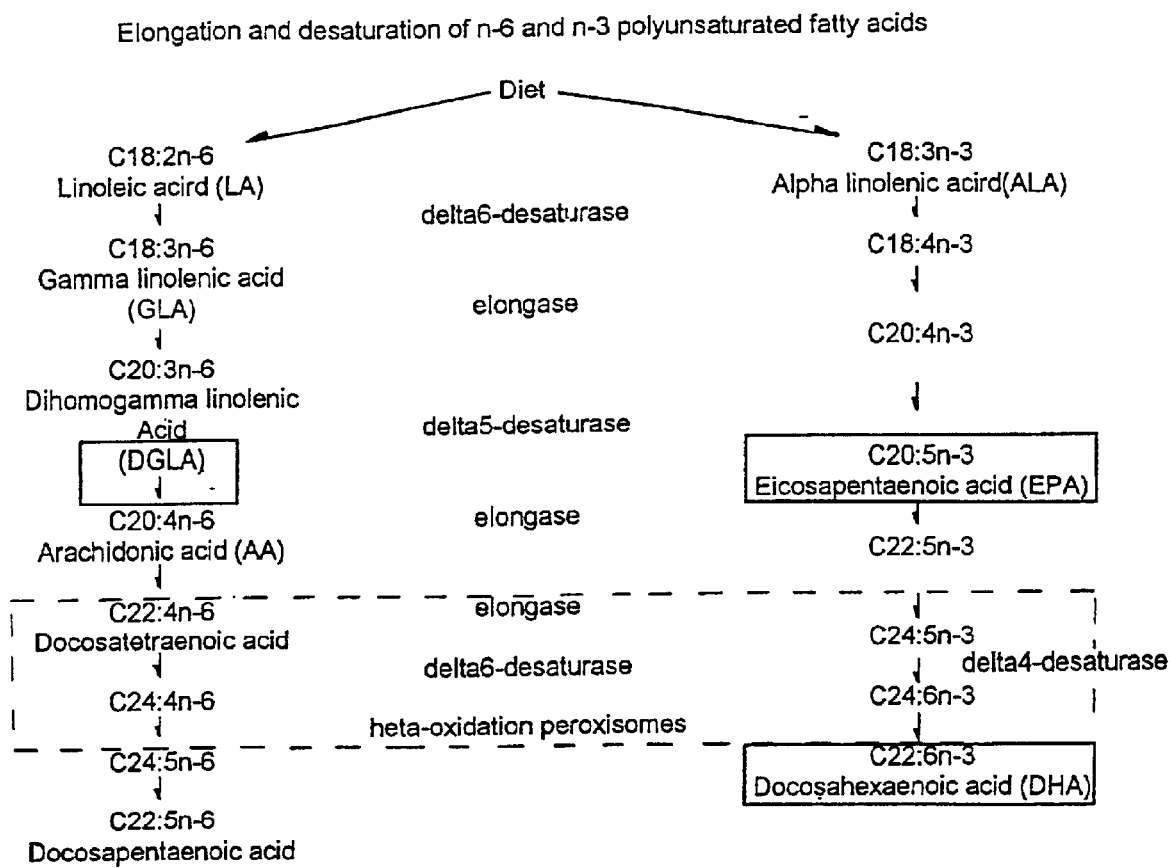

FIG. 2 shows the elongation and desaturation of n-6 and n-3 polyunsaturated fatty acids.

Figure 3:
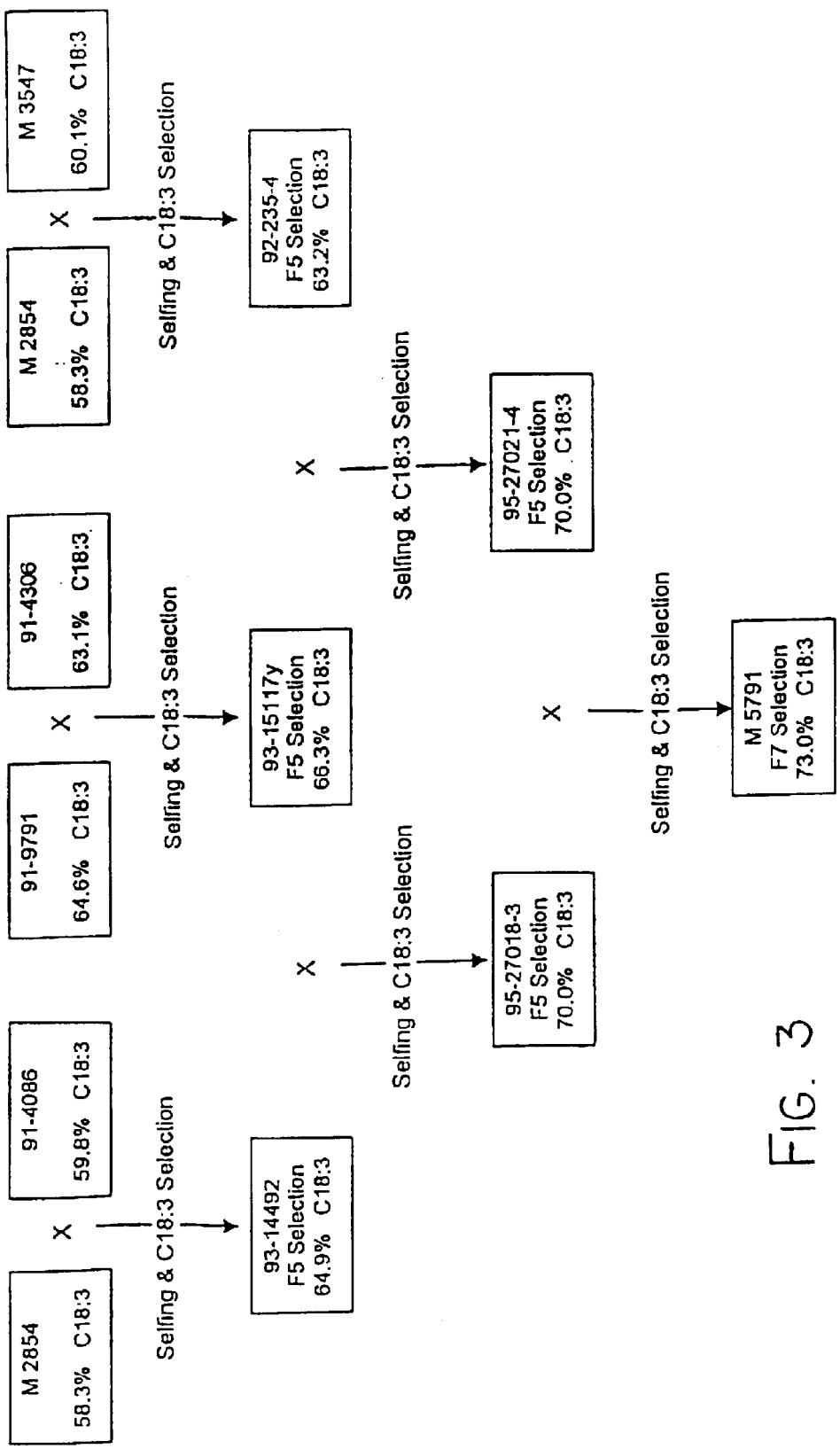

FIG. 3 shows the pedigree of high linolenic flax M 5791.

Figure 4:
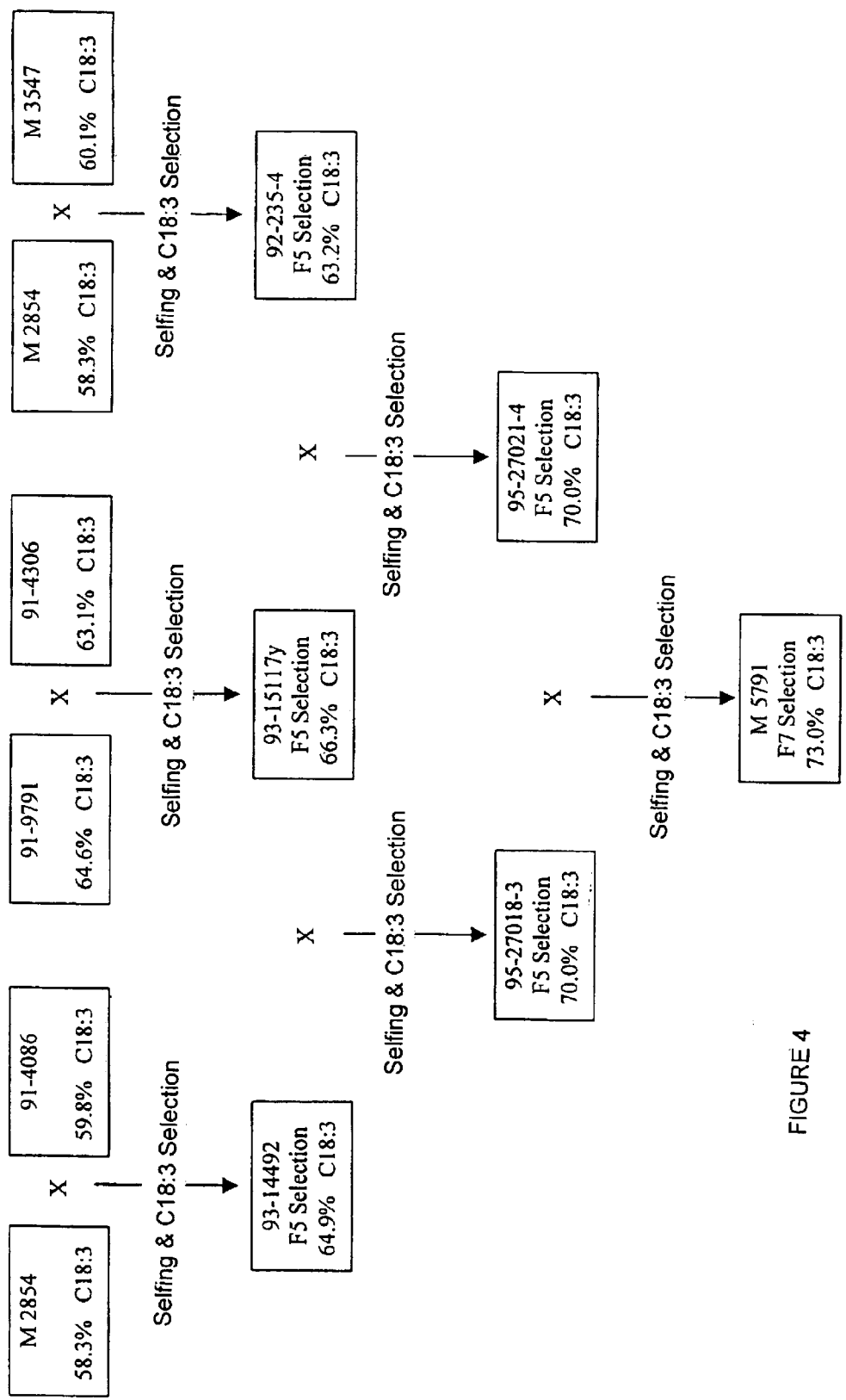

FIG. 4 shows the crosses used to generate M5791.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

DEFINITIONS

As used herein, "high linolenic flax" refers to flax seeds or plants wherein the percentage of total fatty acid content that is linolenic acid is greater than 65%.

As used herein, "inflammatory disease" refers to diseases that are associated with an inappropriate or over-activation of the inflammation cascade.

As used herein, "autoimmune disorder" refers to diseases characterized by destruction of host tissue by the host immune system.

The invention relates to flax seeds, plants or products made therefrom wherein linolenic acid is greater than 65% of the total fatty acid content. In some embodiments, the linolenic acid content may be greater than 70% of the total fatty acid content. In yet other embodiments, the linolenic acid content may be 70–80% or 70–75% of the total fatty acid content.

As discussed herein, the crossing of flax lines has produces a high linolenic flax line, designated M5791 (ATCC # PTA-5755). As shows in Tables 4 and 5, M5791 shows much higher linoleic acid content relative to other flax lines.

As will be appreciated by one knowledgeable in the art, and as discussed herein, growth conditions can affect linolenic acid content. However, flax line M5791 can be grown and processed using means known in the art for growing and processing flax.

The linolenic content of M 5791 oil is not altered by any methods of extraction of oil from seed, i.e. solvent, cold press, or distillation.

As discussed above, flax and/or linseed oil have are present in a number of industrial, nutritional and medicinal products.

For example, linseed oil is used as an industrial oil because of its drying properties, which are in turn directly proportional to the linolenic acid content. Industrial uses of this oil include but are by no means limited to the manufacture of brake linings, adhesives, manufacture of hardboard and fibreboard, protective coatings, paints, house paint primers, varnishes, lacquers, stains, alkyd resins, enamels, epoxidized oils, floor coverings, linoleum, oilcloth, tarpaulin and other coated fabrics, patent leather, industrial chemical, fatty acids, soap, glycerin, printing inks, grinding oils, newsprint, core oils, caulking compounds, waterproofing compounds, mastic cements, foundry binders, brake lining, hardboard, shoe polish, herbicide, pesticide carrier, antispalling and curing treatments for concrete, tempering oil, bonding oil, and highly conjugated oils for hardboards and the like. Thus, use of linseed oil from high linolenic acid flax will result in, for examples, faster drying paints, coatings, inks and the like. Examples of industrial uses of linseed oil include but are by no means limited to U.S. Pat. Nos. 5,965,633, 5,693,715, 5,653,789, 3,488,202 and 4,002,585.

Furthermore, the meal remaining from the flax seed oil extraction processes described above also has industrial purposes, for example, in animal feed or pet food. As will be appreciated by one knowledgeable in the art, meal from the high linolenic acid flax seeds may be used in any application known in the art for using meal from flax seeds, wherein the meal has the added benefit of having a higher linolenic acid content.

The above-described flax seed may be used, for example, to produce high protein animal feed. For example, the seed, oil, or meal may be used in feed for dairy and beef cattle, swine and/or poultry to increase levels of linolenic acid in the resulting food products, for example, eggs, meat and milk. As discussed above, the seed and meal may also be used in pet foods. The seed and oil may also be used as a source of linolenic acid for growing fish.

As discussed above, polyunsaturated fats, for example, linolenic acid are essential fatty acids and are required for increased metabolism, oxygen uptake, and energy production. As such, nutritional supplements or food products containing material produced or processed from the high linolenic acid flax line would be higher in polyunsaturated fats and therefore of greater benefit. As such, the high linolenic flax line, seeds or products derived therefrom can be used in, for example, nutritional supplements, food products for human consumption, pet foods and animal feeds. Examples of edible products include, but are by no means limited to, cakes, muffins, bread products (whole seed or flour), replacement for sesame seed in baking products, or cooked and dry cereals Examples of the use of linolenic acid or flax products in nutritional supplements or food products include but are by no means limited to U.S. Pat. Nos. 5,069,903 and 6,060,101.

As discussed above, linolenic acid also plays a role in the prevention and/or treatment of a number of diseases, including, for example, coronary artery disease, hypertension, diabetes, arthritis and other inflammatory or autoimmune disorders. In these embodiments, supplements or pharmaceutical compositions including material derived from the high linolenic acid flax are prepared and used to treat and/or prevent the above-referenced diseases or disorders. Examples of medicinal uses for flax and/or linseed oil include but are by no means limited to U.S. Pat. Nos. 5,859,055, 4,415,554, 5,468,776 and 4,058,594.

In these embodiments, the high linolenic linseed oil or high linolenic flax may be included in a tablet, capsule, tincture, salve, paste, cream or the like.

In some embodiments, the high linolenic acid flax or linseed oil therefrom at therapeutically effective concentrations or dosages may be combined with a pharmaceutically or pharmacologically acceptable carrier, excipient or diluent, either biodegradable or non-biodegradable. Exemplary examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty add esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches. See, for example, *Remington: The Science and Practice of Pharmacy* (20$^{th}$ Edition), 2000, Gennaro, AR ed., Eaton, Pa.: Mack Publishing Co.

In yet other embodiments, oil from the seeds of the high linolenic acid flax plants are used as carriers or diluents for other pharmaceutical or medicinal compounds.

As will be apparent to one knowledgeable in the art, specific carriers and carrier combinations known in the art may be selected based on their properties and release characteristics in view of the intended use.

Thus, the high linolenic acid flax line, seeds therefrom or products derived therefrom can be used in the production of any flax-containing products known in the art. As will be appreciated by one knowledgeable in the art, these products will have the added benefit of having a higher linolenic acid content.

As will be appreciated by one knowledgeable in the art, the flax plant designated M5791 can be used to perform genetic crosses with other flax lines using means known in the art.

The invention will now be described by way of examples, although the invention is in no way limited to the examples.

EXAMPLE I

Breeding Method

High Linolenic flax was developed by conventional plant breeding, ie. hybridization using cultivars, breeding lines and accessions, and selections for high linolenic acid content in segregating populations from crosses, at the AAFC Morden Research Centre, Morden, MB. The development of High Linolenic flax involved 6 crosses. In each of the crosses, the F2 and subsequent generations of crosses were advanced to the F7 generation using the pedigree method of breeding. Selection for high linolenic was initiated in the F2 generation. F2 plants were analyzed on a half-seed basis by gas-liquid chromatography of the fatty acid esters using the method described by Daun et al, J. Amer. Oil Chemists' Society, 60, 1983. Using the remainder of the seed, the F3 generation of high linolenic genotypes were grown in the greenhouse. Single plant selections were made in the F4 generation on basis of linolenic content. The F5 generation of selected lines was grown in a winter nursery. F6 lines were selected for high linolenic content at Morden and seed harvested in bulk. Seed of F7 lines was increased in a winter nursery. High linolenic flax was evaluated in replicated trials conducted in 1998, 1999 and 2000, and in field trials conducted in 1998 and 1999 (Table 5).

Cross $F_1$ —greenhouse
$F_2$ —field; high linolenic genotypes selected by ½ seed analysis
$F_3$ —greenhouse
$F_4$ —field; plants selected for high linolenic content
$F_5$ —winter nursery
$F_6$ —field; lines selected for high linolenic and seed harvested in bulk
$F_7$ —Seed increase in winter nursery
$F_8$ —Replicated trials in Manitoba
$F_9$ —Replicated trials in Manitoba and field trials in Manitoba and Alberta
  93-14492/93-15117y/3/92-235-4/93-15117y
  93-14492—NorLin/5173 (M 2854)//Culbert/FP 827 (91-4086)
  93-15117y—AC Linora/427-2 (91-9791)//NorLin/Szegedi 62 (91-4306)
  92-235-4—NorLin/5173 (M 2854)//McGregor/FP 842 (M 3547)

Date of crosses:

| | |
|---|---|
| Crosses 1 & 2 | -1993 |
| Cross 3 | -1995 |

Pedigree/origin of Parents in crosses:

| Cultivars | Origin |
|---|---|
| AC Linora[1] | AAFC |
| AC McGregor[2] | AAFC |
| NorLin[3] | AAFC |
| Raja | AAFC |
| Redwood 65[4] | U. of Saskatchewan, Saskatoon, SK |
| Culbert[5] | U. of Minnesota, St. Paul, Minn. |

Lines (developed by AAFC)

| | |
|---|---|
| 5173 | -McGregor//Redwood 65/High Oil Line/3/Cl 2941 |
| FP 827 | -McGregor/3/Redwood 65/Valuta/Raja |
| FP 842 | -Cl 2847/Culbert |
| Accessions | Origin |
| Szegedi 62 | Hungary |
| Valuta | Sweden |
| Cl 2847 | USA |
| Cl 2941 | USA |
| 427-2 | Argentina |
| High Oil Line | Unknown |

Description of Cultivars
[1]Can. J. Plant Sci. 73:839–841, 1983
[2]Can. J. Plant Sci. 66:175–176, 1986
[3]Can. J. Plant Sci. 66:171–173, 1986
[4]Can. J. Plant Sci. 45:515–516, 1965
[5]Crop Sci. 17:823, 1977

While the preferred embodiments of the invention have been described above, it will be recognized and understood that various modifications may be made therein, and the appended claims are intended to cover all such modifications which may fall within the spirit and scope of the invention.

| | Uses of Flax |
|---|---|
| Linseed Oil (High Linolenic Acid) Raw & Refined Boiled & Blown Grinding Oils Heat Boiled (polymerized oils) | Adhesives, i.e. manufacture of hardboard and fibreboard Protective Coatings: paints, house paint primers, varnishes, lacquers, stains, alkyd resins, enamels, epoxidized oils Floor Covering: linoleum Oilcloth, tarpaulin and other coated fabrics Patent leather Industrial Chemicals: fatty acids, soap, glycerin Printing inks, grinding oils, newsprint, core oils, caulking compounds, waterproofing compounds, mastic cements, foundry binders, brake lining, hardboard, shoe polish, herbicide and pesticide carrier Antispalling and curing treatments for concrete Tempering oil, bonding oil, and highly conjugated oils for hardboards |
| Seed | Specialty Edible Products: -cakes, muffins -bread products (whole seed or flour) -replacement for sesame seed in baking products -cooked and dry cereals |
| Seed & Oil | Health Food: -source of linolenic acid -to make pills -inclusion in pharmaceutical mediator mutations |
| Linseed Meal | High protein animal feed Seed, oil, meal: Dairy and beef cattle, swine and poultry feed and also to increase levels of linolenic acid in food products, i.e. eggs, meat and milk Pet Foods: seed and meal Fish feed in fish culture: Seed and oil-source of linolenic acid required by growing fish, i.e. salmon |

TABLE 1

Fatty Acid Composition of Major Seed Oils

| | Fatty Acid Content % | | | |
|---|---|---|---|---|
| | Saturates | Oleic | Linoleic | Linolenic |
| Linseed Flax | 9 | 20 | 13 | 58 |
| Canola | 6 | 58 | 26 | 10 |
| Safflower | 9 | 20 | 70 | <1 |
| Sunflower | 11 | 20 | 69 | — |
| Corn | 13 | 25 | 61 | 1 |
| Olive | 14 | 77 | 8 | 1 |
| Soybean | 15 | 24 | 54 | 7 |
| Peanut | 18 | 48 | 34 | — |
| Cottonseed | 27 | 19 | 54 | — |

Source: Agricultural Handbook No. 8-4. Human Nutr. Inform. Serv., U.S. Dept. Agric., Washington, DC. 1979.

TABLE 2

Fatty Acid Composition of Linseed Flax and High Linolenic Flax (M 5791)

| Fatty acid, % in oil | | Linseed Flax | High Linolenic Flax |
|---|---|---|---|
| Palmitic | C16:0 | 5.4 | 4.5 |
| Stearic | C18:0 | 3.1 | 2.2 |
| Oleic | C18:1 | 17.1 | 9.7 |
| Linoleic | C18:2 | 14.7 | 10.8 |
| Linolenic | C18:3 | 59.6 | 72.8 |
| Iodine value | | 196 | 217 |

TABLE 3

Linolenic Acid Content of Canadian Flaxseed by Province-1992–1999*

| | Manitoba | Saskatchewan | Alberta | Mean |
|---|---|---|---|---|
| 1992 | 59.1 | 58.7 | 55.7 | 58.8 |
| 1993 | 57.9 | 61.0 | 60.7 | 59.7 |
| 1994 | 58.6 | 60.5 | 56.9 | 59.6 |
| 1995 | 55.8 | 59.4 | 60.8 | 58.1 |
| 1996 | 57.8 | 59.3 | 59.8 | 58.7 |
| 1997 | 58.8 | 57.4 | 58.9 | 58.0 |
| 1998 | 57.2 | 56.6 | 56.9 | 56.8 |
| 1999 | 60.4 | 59.4 | 59.0 | 59.6 |
| Mean | 58.2 | 59.0 | 58.6 | 58.7 |

Source: Quality of Western Canadian flaxseed, Grain Research Laboratory, Canadian Grain Commission, Winnipeg, MB. Linolenic acid determined by gas chromatography of methyl esters of fatty acids according to international Organization for Standardization; Animal and vegetable fats and oils 1505508:1990E.

TABLE 4

Linolenic Acid Content of Four Widely Grown Canadian Flax Cultivars in Flax Cooperative Tests* conducted at Eight Locations in Manitoba and Saskatchewan, 1995–1999.

| | Manitoba | | | | Saskatchewan | | | | |
|---|---|---|---|---|---|---|---|---|---|
| | | Protage la Prairie | | | | | | | |
| | Morden | Prairie | Rosebank | Brandon | Indian Head | Melfort | Saskatoon | Scott | Mean |
| 1995 | | | | | | | | | |
| AC McDuff | 52.5 | 53.8 | 53.5 | 49.0 | 57.2 | 56.2 | 54.9 | 56.2 | 54.2 |
| CDC Normandy | 54.0 | 55.7 | 55.8 | 52.8 | 60.2 | 56.8 | 56.5 | 58.7 | 56.3 |
| Flanders | 55.0 | 56.5 | 56.3 | 52.0 | 60.2 | 58.9 | 57.5 | 58.9 | 56.9 |
| NorLin | 53.8 | 55.4 | 54.5 | 53.1 | 60.0 | 56.7 | 56.5 | 58.9 | 56.1 |
| Mean | 53.8 | 55.4 | 55.0 | 51.7 | 59.4 | 57.1 | 56.3 | 58.2 | 55.9 |
| 1996 | | | | | | | | | |
| AC McDuff | 53.6 | 55.2 | 55.5 | 52.6 | 55.4 | 53.8 | 54.4 | 56.0 | 54.6 |
| CDC Normandy | 55.8 | 54.6 | 57.6 | 54.9 | 58.2 | 56.7 | 56.4 | 58.1 | 56.5 |
| Flanders | 57.3 | 58.3 | 58.0 | 54.3 | 57.8 | 56.2 | 56.8 | 558.7 | 57.2 |
| NorLin | 55.2 | 54.2 | 56.8 | 54.7 | 57.8 | 55.4 | 56.0 | 57.7 | 56.0 |
| Mean | 55.5 | 55.6 | 57.0 | 54.1 | 57.3 | 55.5 | 55.9 | 57.6 | 56.0 |
| 1997 | | | | | | | | | |
| AC McDuff | 53.3 | 55.4 | 56.0 | 52.2 | 49.7 | 53.1 | 52.1 | 50.6 | 52.8 |
| CDC Normandy | 53.0 | 55.0 | 58.0 | 52.1 | 52.9 | 51.6 | 55.1 | 54.3 | 54.0 |
| Flanders | 55.9 | 58.9 | 58.1 | 53.8 | 53.9 | 54.8 | 55.1 | 53.7 | 55.5 |
| NorLin | 52.9 | 56.8 | 57.7 | 53.1 | 51.9 | 52.5 | 55.4 | 53.9 | 54.3 |
| Mean | 53.8 | 56.5 | 57.4 | 52.8 | 52.1 | 53.0 | 54.4 | 53.1 | 54.1 |

TABLE 4-continued

Linolenic Acid Content of Four Widely Grown Canadian Flax Cultivars in Flax Cooperative Tests* conducted at Eight Locations in Manitoba and Saskatchewan, 1995–1999.

| | Manitoba | | | | Saskatchewan | | | | |
|---|---|---|---|---|---|---|---|---|---|
| | Morden | Protage la Prairie | Rosebank | Brandon | Indian Head | Melfort | Saskatoon | Scott | Mean |
| 1998 | | | | | | | | | |
| AC McDuff | 51.5 | 51.9 | 51.4 | 46.9 | 50.8 | 47.9 | 49.5 | 45.5 | 49.5 |
| CDC Normandy | 53.8 | 53.2 | 53.2 | 48.9 | 53.7 | 51.4 | 52.3 | 48.2 | 51.8 |
| Flanders | 52.6 | 54.3 | 54.6 | 49.7 | 53.5 | 52.7 | 53.0 | 47.8 | 52.3 |
| NorLin | 52.7 | 53.5 | 54.0 | 49.8 | 53.4 | 50.0 | 51.3 | 48.0 | 51.6 |
| Mean | 52.6 | 53.2 | 53.3 | 48.8 | 52.8 | 50.7 | 51.5 | 47.4 | 51.3 |
| 1999 | | | | | | | | | |
| AC McDuff | 57.1 | 58.8 | 59.2 | 58.4 | 59.8 | 53.4 | 51.6 | 52.0 | 56.3 |
| CDC Normandy | 59.9 | 59.0 | 60.0 | 58.2 | 60.1 | 53.5 | 56.1 | 55.5 | 57.8 |
| Flanders | 60.2 | 61.1 | 62.4 | 49.0 | 61.4 | 54.6 | 54.7 | 55.6 | 58.7 |
| NorLin | 59.4 | 59.0 | 59.8 | 58.8 | 59.4 | 53.3 | 55.4 | 54.9 | 57.5 |
| Mean | 59.1 | 59.6 | 60.3 | 58.6 | 60.2 | 53.7 | 54.4 | 54.5 | 57.6 |
| Overall Mean | 55.0 | 56.0 | 56.6 | 53.2 | 56.4 | 54.0 | 54.5 | 54.2 | |

*Cooperative tests conducted by Prairie Registration Recommending Committee on Grain. Linolenic acid content determined by gas-liquid chromatography of the fatty acid esters using the method described by Daun et al., J. Amer. Oil Chemists' Society, 60, 1983.

TABLE 5

Linolenic Acid Content* of High Linolenic Flax (M 5791) in Replicated Trials in Manitoba, 1998 & 1999, in Comparison with Three Commercial Cultivars

| | Morden | Burdick | Portage la Prairie |
|---|---|---|---|
| 1998 | | | |
| High Linolenic Flax | 70.1 | | |
| AC Emerson | 57.0 | | |
| Flanders | 53.1 | | |
| NorLin | 55.2 | | |
| 1999 | | | |
| Test 1 | | | |
| High Linolenic Flax | 70.9 | 71.9 | 72.7 |
| AC Emerson | 61.7 | 60.6 | 65.1 |
| Flanders | 60.4 | 60.6 | 62.5 |
| NorLin | 59.7 | 57.8 | 59.3 |
| Test 2 | | | |
| High Linolenic Flax | 71.9 | 70.3 | |
| AC Emerson | 58.6 | 59.2 | |
| Flanders | 58.2 | 60.3 | |
| NorLin | 56.9 | 59.3 | |
| Test 3 | | | |
| High Linolenic Flax | 72.0 | 71.3 | |
| AC Emerson | 60.5 | 61.6 | |
| Flanders | 60.0 | 60.9 | |
| NorLin | 58.6 | 58.2 | |

*Linolenic acid content determined by gas-liquid chromatography of the fatty acid esters using the method described by Daun et al., J. Amer. Oil Chemists' Society, 60, 1983.

TABLE 6

Linolenic Acid Content of High Linolenic Flax (M 5791) in Field Trials, 1998 & 1999

| Location | Year | | % Linolenic Content |
|---|---|---|---|
| Fisher Branch, MB | 1998 | | 72.7 |
| | | Field 1 | 72.7 |
| | 1999 | Field 2 | 72.2 |
| Erickson, MB | 1998 | | 72.9 |
| | | Field 1 | 72.9 |
| | 1999 | Field 2 | 72.9 |
| Gadsby, AB | 1998 | | 72.6 |
| | | Field 1 | 72.6 |
| | 1999 | Field 2 | 73.1 |

What is claimed is:

1. A flax seed that is the product of a plant line designated M5791 (American Tissue Culture Collection Deposit #PTA-5755), wherein the linoleic acid content of said flax seed is greater than 70%.

2. A flax plant designated M5791 (American Tissue Culture Collection Deposit #PTA-5755), wherein the linolenic acid content of said flax seed is greater than 70%.

3. Progeny of a flax plant designated M5791 (American Tissue Culture Collection Deposit #PTA-5755), wherein said progeny produce seeds having a linolenic acid content of greater than 70% of the total fatty acid content of said seed.

4. The progeny according to claim 3 wherein the linolenic acid content is between 70%–80%.

5. Seed from the flax plant of claim 4.

6. A method of producing a flax plant line comprising the steps of:

(a) crossing a plant of flax plant line designated M5791 (American Tissue Culture Collection Deposit # PTA-5755), wherein the linoleic acid content of said flax seeds is greater than 70%, or progeny thereof, with agronomically elite flax plant; and (b) selecting at least one descendant of said cross, said descendant producing seeds having a linoleic acid content of greater than 70% relative to the total fatty acid content of said seed.

7. The progeny according to claim 3 wherein the linoleic acid content in between 70%–75%.

8. The progeny according to claim 6 wherein the linoleic acid content in between 70%–80%.

9. The progeny according to claim 6 wherein the linoleic acid content in between 70%–75%.

* * * * *